US008772317B2

(12) United States Patent
Masuda

(10) Patent No.: US 8,772,317 B2
(45) Date of Patent: Jul. 8, 2014

(54) AQUEOUS PHARMACEUTICAL SUSPENSIONS CONTAINING REBAMIPIDE AND MANUFACTURING PROCESS THEREOF

(75) Inventor: Yoshito Masuda, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 262 days.

(21) Appl. No.: 12/447,065

(22) PCT Filed: Oct. 24, 2007

(86) PCT No.: PCT/JP2007/071167
§ 371 (c)(1),
(2), (4) Date: Apr. 24, 2009

(87) PCT Pub. No.: WO2008/050896
PCT Pub. Date: May 2, 2008

(65) Prior Publication Data
US 2010/0029714 A1  Feb. 4, 2010

(30) Foreign Application Priority Data
Oct. 26, 2006  (JP) .................................. 2006-291535

(51) Int. Cl.
*A01N 43/42* (2006.01)
*A61K 31/47* (2006.01)
*A01N 57/00* (2006.01)
*A61K 31/675* (2006.01)

(52) U.S. Cl.
USPC .......................................... 514/312; 514/89

(58) Field of Classification Search
USPC ........................................................ 514/312
See application file for complete search history.

(56) References Cited

U.S. PATENT DOCUMENTS

| 5,188,826 A * | 2/1993 | Chandrasekaran et al. ................ 424/78.04 |
| 5,366,985 A | 11/1994 | Nakayama et al. |
| 5,556,848 A | 9/1996 | Kimura et al. |
| 6,060,486 A | 5/2000 | Urashima et al. |
| 6,274,634 B1 | 8/2001 | Yasueda et al. |
| 6,780,882 B2 * | 8/2004 | Phillips .................... 514/338 |
| 6,884,768 B2 * | 4/2005 | Kimura et al. ................ 514/1 |
| 2005/0255144 A1 | 11/2005 | Schultz |
| 2006/0074053 A1 | 4/2006 | Asada et al. |

FOREIGN PATENT DOCUMENTS

| JP | 8-217678 | 8/1996 |
| JP | 9-504294 | 4/1997 |
| JP | 9-301866 A | 11/1997 |
| JP | 10-510532 | 10/1998 |
| JP | 11-029463 | 2/1999 |
| JP | 2005-8625 A | 1/2005 |
| WO | WO 92/17174 | 10/1992 |
| WO | WO 95/11669 | 5/1995 |
| WO | WO 96/16659 | 6/1996 |
| WO | WO 2006/028270 A1 | 3/2006 |
| WO | WO 2006/052018 A1 | 5/2006 |
| WO | WO 2007/132907 A1 | 11/2007 |

OTHER PUBLICATIONS

Interaction of leptin with gastric myofibroblast transdifferentiation in Helicobacter pylori-infected Mongolian gerbils: the effect of rebamipide Aliment Pharmacol Ther 2003; 18 (Suppl. 1): 99-105.).*

* cited by examiner

*Primary Examiner* — Layla Soroush
(74) *Attorney, Agent, or Firm* — Finnegan, Henderson, Farabow, Garrett & Dunner, L.L.P.

(57) ABSTRACT

The invention provides a rebamipide-containing aqueous pharmaceutical suspension which can be prepared by a simple process and keep the dispersed fine-particle state of rebamipide stable without having the fine particle agglutinated. The rebamipide-containing aqueous pharmaceutical suspension of the invention is prepared by mixing polyvinyl alcohol and additionally a sodium salt compound with rebamipide.

5 Claims, 1 Drawing Sheet

A
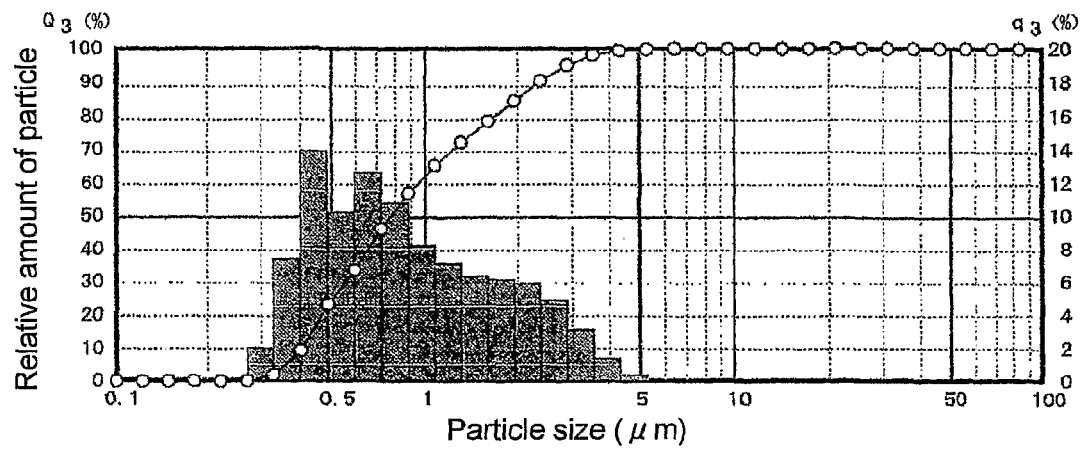
B
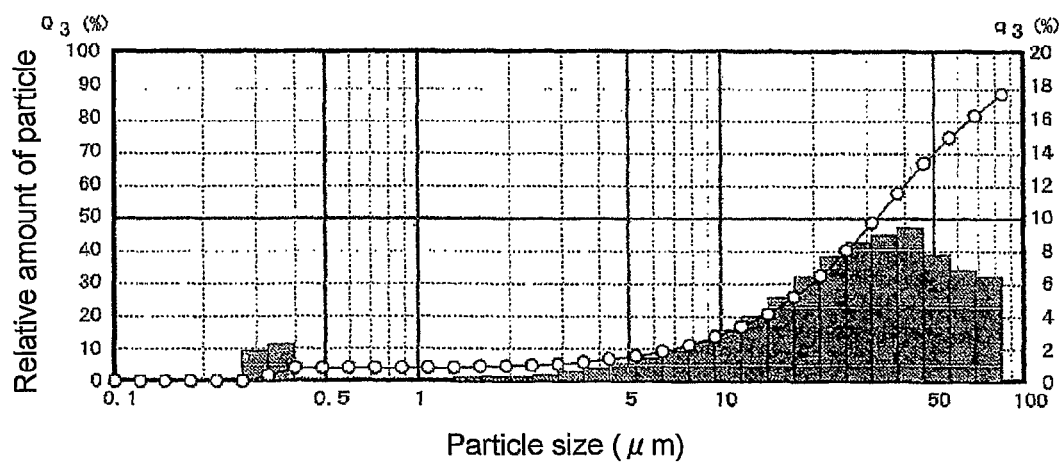

AQUEOUS PHARMACEUTICAL SUSPENSIONS CONTAINING REBAMIPIDE AND MANUFACTURING PROCESS THEREOF

TECHNICAL FIELD

The invention relates to a rebamipide-containing aqueous pharmaceutical suspension which can be prepared by a simple process and keep the dispersed fine-particle state of rebamipide stable; and a process thereof.

BACKGROUND OF THE INVENTION

Rebamipide exhibits anti-inflammatory and anti-ulcer effects in gastrointestinal tract and now has been used as a pharmaceutical. In addition, rebamipide has an increasing action of goblet cell density in cornea and conjunctiva of eyes, which increases the yield of mucin that is an ingredient of mucus and the secretion of mucus and lacrimal fluid, and hereby the cornea and conjunctiva can be protected or stabilized. Therefore, rebamipide is known to be effective in preventing and treating the eye disease caused by dryness of cornea which is appellatively referred as dry eye (JP-A-9-301866).

However, rebamipide does not have a sufficient and long-term-stable solubility in the physiologically neutral pH range where the irritant and dysfunctional demerit for eyes or mucosal tissue is low, and hence it is impossible to prepare a rebamipide-formulation as a water solution, because rebamipide is an acidic compound. Alternatively, it is possible to prepare a water-solution of rebamipide using a surfactant such as an ionic surfactant and a non-ionic surfactant, or a solubilizer such as a cyclodextrin derivative. When administering the formulation, however, such surfactant or such solubilizer might have a biological ingredient in the mucosa dissolved in the solution and might interfere with the activity of rebamipide, which is an action of stabilizing and protecting the mucosa.

On the contrary, using an aqueous pharmaceutical suspension containing a dispersed rebamipide, the above-mentioned demerit as to the low solubility of rebamipide will be overcome and hence it will be possible to prepare a rebamipide-formulation. However, rebamipide usually exists in a powder-form prepared by agglutinating a needle crystal of rebamipide (primary particle, mean particle size: short gage length 0.1-0.5 μm, long gage length 0.2-4 μm) to form a secondary particle thereof (mean particle size: about 10-50 μm), and therefore it is thought to be hard to prepare a suspension of rebamipide from a fine particle of rebamipide. Under the prior art, therefore, in order to equally disperse as a fine particle the agglutinated rebamipide that is a secondary particle, it had been indispensable to add a cellulose derivative that is a water-soluble polymer known as a suspending agent, a surfactant and so on to the mixture containing rebamipide, and further to strongly stir the mixture using a special dispersing/suspending device such as a high pressure homogenizer, a colloid mill, a turbine-type stirring device, a high-speed rotary shear stirring device, and an ultrasonicator.

Furthermore, even if it is possible to disperse rebamipide as a fine particle in an aqueous solution, there are some problems in the prior art, namely, the fine particle of rebamipide will be re-agglutinated as the reserve time passes to re-form the secondary particle or to enlarge the crystalline particle, and the precipitated suspension-particle is not easily re-dispersed as a fine particle.

Under such a background of the prior art, it has been desired to develop an aqueous pharmaceutical suspension containing rebamipide so that rebamipide can be stably dispersed as a fine particle using a simple method and the fine particle cannot be re-agglutinated

DISCLOSURE OF INVENTION

Problem to be Solved by the Invention

The invention has been found in order to overcome the above-mentioned problems of the prior art. The invention provides a rebamipide-containing aqueous pharmaceutical suspension which can be prepared by a simple process and keep the dispersed fine-particle state of rebamipide stable without having the fine particle agglutinated. It is a purpose of the invention.

Means to Solve the Problem

The present inventors have extensively studied to reach the above object and then have found that the addition of polyvinyl alcohol together with rebamipide to an aqueous solution get a fine particle of rebamipide equally dispersed in the aqueous solution without a specific dispersing or suspending device and the resulting suspension can be stored as a stable suspended state without re-agglutinating the fine particle of rebamipide. Based upon the new findings and further additional improvements, the present invention has been completed.

The invention provides an aqueous pharmaceutical suspension comprising rebamipide and a process for the preparation thereof as mentioned below.

[1] An aqueous suspension comprising rebamipide and polyvinyl alcohol.

[2] The aqueous suspension of [1] further comprising a sodium salt compound.

[3] The aqueous suspension of [1] or [2] wherein rebamipide is in 0.1-30 w/v % and polyvinyl alcohol is in 0.1-4 w/v %.

[4] The aqueous suspension of any one of [1]-[3], which is an ophthalmic formulation.

[5] A process for the preparation of an aqueous suspension comprising rebamipide, which comprises (1) the first step: mixing water and polyvinyl alcohol to prepare a aqueous solution containing polyvinyl alcohol, and (2) the second step: adding rebamipide to the aqueous solution containing polyvinyl alcohol given in the first step and mixing the mixture to give the aqueous suspension comprising rebamipide.

Effect of the Invention

According to the aqueous pharmaceutical suspension of the invention, rebamipide is equally dispersed as a fine-particle state and the resulting suspension can be stored as a stably-dispersed state without re-agglutinating the fine particle of rebamipide and enlarging the crystalline particle even when storing it for long term. Even when rebamipide precipitates, it is possible that the equally-dispersed state of the fine-crystalline particle is easily recovered with shaking by hand.

Additionally, the aqueous pharmaceutical suspension of the invention comprises polyvinyl alcohol, and hence it is not necessary to use a dispersing/suspending device for strong stir such as a homogenizer, a colloid mill, a turbine-type stirring device, a high-speed rotary shear stirring device, and an ultrasonicator and it is enough to use a usual agitation, i.e. just mixing in order to disperse the rebamipide which had been agglutinated to form a secondary particle into a fine-particle state. Therefore, the aqueous pharmaceutical suspension of the invention also has a merit on the preparation to be formulated via a simple process.

BRIEF DESCRIPTION OF THE DRAWINGS

FIG. 1 shows results that the particle distribution of rebamipide is measured in Experiment 2 (Q3: cumulative distribution (%), line graph; q3: frequency distribution (%), bar graph) In FIG. 1, "A" indicates the particle distribution of rebamipide suspension in Example 12, and the "B" indicates the particle distribution of rebamipide suspension in Comparative Example 1.

DETAILED DESCRIPTION OF THE PREFERRED EMBODIMENTS

The aqueous pharmaceutical suspension of the invention comprises rebamipide as a pharmaceutically active ingredient.

The powder of rebamipide active ingredient used in the invention generally exists in a secondary particle state (mean particle size: about 10-50 μm) which is formed by agglutinating a primary particle of rebamipide (a needle crystal, mean particle size: short gage length 0.1-0.5 μm, long gage length 0.2-4 μm). In the aqueous pharmaceutical suspension of the invention, the existence of polyvinyl alcohol enables rebamipide to retain as a stably-dispersed state wherein rebamipide is dispersed as a fine particle whose mean particle size is 0.1-10 μm, preferably 0.2-5 μm. Herein, the mean particle size (μm) can be calculated according to the following method. That is, using the data of the particle distribution which is measured by a laser diffraction-scattering, the range of the particle size (maximum particle size: $x_1$, minimum, particle size: $x_{n+1}$) is divided into "n", which is calculated according to the following formula to give a mean value thereof. The value is defined as "mean particle size".

Mean value=$10^\mu$
wherein $$\mu = \frac{1}{100}\sum_{j=1}^{n} q_j \left( \frac{\log_{10} x_j + \log_{10} x_j + 1}{2} \right)$$

$x_j$: Particle size,
$q_j$: Deference % (frequency distribution).

The content amount of rebamipide in the aqueous pharmaceutical suspension of the invention can be suitably set in response to the body-site for treatment, the manner of administration and so on; for example, preferably 0.1-30 w/v %, more preferably 0.3-10 w/v %.

Furthermore, the aqueous pharmaceutical suspension of the invention comprises polyvinyl alcohol to have the above rebamipide stably-dispersed as a fine-particle state.

The saponification degree of polyvinyl alcohol used in the invention is not limited, and a partly-saponified or completely-saponified polyvinyl alcohol can be used, and, a partly-saponified polyvinyl alcohol is preferable because a partly-saponified one makes the dispersibility of rebamipide enhanced much more. The polyvinyl alcohol used in the invention includes a partly-saponified one having mean saponification degree of preferably 70-94% (mol), most preferably 85-90% (mol). The mean saponification degree is given by the measure according to JIS K 6726 3.5.

The water-soluble viscosity of polyvinyl alcohol used in the invention (20° C., concentration: 4 w/w % water-soluble viscosity, hereinafter denoted as "viscosity at 4%/20° C.") is, but not limited thereto, preferably 3-110 mPa·s, especially 20-60 mPa·s. The viscosity at 4%/20° C. mentioned herein is a measurable value according to the viscosity determination described in the Japanese Pharmacopoeia XIV (General Tests, Viscosity Determination, Method I Viscosity measurement by capillary tube viscometer). The practical process is shown as follows: (1) to prepare 4 w/w % polyvinyl alcohol in water, which is charged in a capillary tube viscometer (Ubbelohde-type viscometer) to keep it in constant-temperature water bath of 20° C. (±0.1° C.) for 20 minutes, (2) to record the time, t(s), required for the meniscus of the sample solution to fall from the upper to the lower marked line of the capillary tube viscometer, and (3) to calculate the viscosity at 4%/20° C. using the following formula with the measured value.

Kinematic viscosity ν=$K$ (viscometer constant, mm²/s²)×$t$ (time for measuring, s)

Viscosity η (viscosity at 4%/20° C.)=ν (kinematic viscosity)×ρ (density of the liquid sample, g/mL)=$K$ (viscometer constant, mm²/s²)×$t$ (time for measuring, s)×ρ(density of the liquid sample, g/mL)

The mixing ratio of polyvinyl alcohol in the aqueous pharmaceutical suspension of the invention can be suitably varied depending on the mixing ratio of rebamipide or the kind of polyvinyl alcohol as used, and for example, it is preferably 0.1-4 w/v %, more preferably 0.3-2 w/v %.

In order to homogeneously- and stably-disperse rebamipide as a fine-particle state, an aqueous pharmaceutical suspension of the invention wherein the mixing ratio between rebamipide and polyvinyl alcohol is applied to the above-mentioned mixing ratio and additionally the mixing ratio of polyvinyl alcohol is 2-4000 by weight, preferably 10-1000 by weight against 100 of rebamipide by weight is exemplified as a preferable embodiment.

In the aqueous pharmaceutical suspension of the invention, rebamipide which is in primary particle state can be prevented much more effectively from being re-agglutinated when the suspension comprises, in addition to rebamipide and polyvinyl alcohol, a metal salt compound and/or a Tris salt compound which are soluble in aqueous solution.

Herein, the metal salt compound which is soluble in aqueous solution is not limited as far as it is pharmaceutically acceptable, including for example, a sodium salt compound such as sodium chloride, disodium hydrogen phosphate, sodium dihydrogen phosphate, sodium succinate, sodium tartrate, sodium hydroxide, sodium acetate, sodium carbonate, and sodium citrate; a potassium salt compound such as potassium chloride, dipotassium hydrogen phosphate, potassium dihydrogen phosphate, potassium succinate, potassium tartrate, potassium hydroxide, potassium acetate, potassium carbonate, and potassium citrate; a calcium salt compound such as calcium chloride, calcium hydroxide, calcium carbonate, and calcium citrate; and a magnesium salt compound such as magnesium chloride, magnesium hydroxide, magnesium carbonate, and magnesium citrate. Also, the Tris salt compound which is soluble in aqueous solution is not limited as far as it is pharmaceutically acceptable, including for example, tris(2-amino-2-hydroxymethyl-1,3-propanediol).

Amongst the metal salt compounds and/or Tris salt compounds, sodium salt compound, especially sodium chloride is preferably used in the aqueous suspension formulation of the invention since it has a potent action to prevent the dispersed rebamipide as a fine-particle state from being re-agglutinated.

The aqueous suspension formulation of the invention may comprise one kind of the metal salt compound and/or Tris salt compound; or 2 or more kinds of the metal salt compounds and/or Tris salt compounds.

In case that the metal salt compound and/or Tris salt compound is added in the suspension, the concentration of said metal salt compound and/or Tris salt compound in the aqueous suspension formulation is not limited and includes, for example, 0.01-3 w/v %, preferably 0.1-2 w/v % in total.

The osmotic pressure of the aqueous suspension formulation of the invention is not limited as far as it is physiologically acceptable. For example, in case that the aqueous suspension formulation of the invention is used in ophthalmic formulation, the osmotic pressure of the formulation used is generally 150-600 mOsm/kg, preferably 200-400 mOsm/kg, more preferably 245-365 mOsm/kg. The osmotic pressure can be adjusted by a manner known in the art with the above-mentioned metal salt compound and/or Tris salt compound; or a sugar, a sugar alcohol, a polyhydric alcohol, etc.

The pH of the aqueous suspension formulation of the invention is not limited as far as it is pharmaceutically acceptable and includes, for example, 3.0-9.0, preferably 5.0-7.0. The pH can be adjusted by a manner known in the art with a pH regulator such as citric acid, phosphoric acid, acetic acid, a salt thereof, hydrochloric acid, and sodium hydroxide.

The aqueous suspension formulation of the invention may include other active pharmaceutical ingredients, a preservative, a refrigerant, a surfactant, a flavor, a coloring agent, a chelator, a buffer, a thickener, etc. in addition to the above-mentioned ingredients as far as they do not interfere in the effect of the invention. The examples of the preservative acceptable in the aqueous suspension formulation of the invention include parabens such as methyl paraben, ethyl paraben, and butyl paraben; quaternary ammoniums such as benzalkonium chloride, and benzethonium chloride; guanidine germicides such as chlorhexidine gluconate; sodium edetate; etc.

The aqueous suspension formulation of the invention is adapted for preferably a formulation for mucosa such as ophthalmic formulation, nasal spray, and inhalant formulation which is an atomized formulation for pulmonary administration sprayed with a spray device for inhalation, and also for oral formulation, injection, etc. The aqueous suspension formulation of the invention is used more preferably as an ophthalmic formulation.

Furthermore, a gelatinizing agent, a thickener, an ointment base, etc. can be added to the aqueous suspension formulation of the invention to formulate a useful gel or ointment form.

The aqueous suspension formulation of the invention can be prepared by mixing a predetermined amount of rebamipide, polyvinyl alcohol, and optional other ingredients with pharmaceutically acceptable water (preferably, purified water or injectable water). As a preferable process for the preparation of an aqueous suspension formulation of the invention, the following process comprising the first step and the second step is exemplified:

(1) the first step: mixing water and polyvinyl alcohol to prepare a aqueous solution containing polyvinyl alcohol, and (2) the second step: adding rebamipide to the aqueous solution containing polyvinyl alcohol given in the first step and mixing the mixture to give the aqueous pharmaceutical suspension comprising rebamipide.

The ingredients other than rebamipide and polyvinyl alcohol may be added in either the first step or the second step. In the second step, it is possible to equally-disperse rebamipide as a fine-particle state just with weak stirring using a general propeller stirrer (unnecessary to use a special strong stirring) since powdered rebamipide in an agglutinated state which forms a secondary particle thereof is very dispersible as a fine particle due to the action of polyvinyl alcohol.

EXAMPLE

Hereinafter, the present invention is further illustrated by the following examples, but should not be construed to be limited thereto. The polyvinyl alcohol used in the following Examples 1-4 and 7-12 is "Poval 224C™", (KURARAY CO., LTD.) (saponification degree: 86-89% (mol), viscosity at 4%/20° C.: 20-48 mPa·s). Further, the polyvinyl alcohol used in the following Examples 5-6 is "Polyvinylalcohol USP™" (Spectrum Quality Product, USA) (saponification degree: δ 6-89% (mol), viscosity at 4%/20° C.: 20-48 mPa·s).

Example 1

Ophthalmic Formulation

| | |
|---|---|
| Rebamipide | 0.100 g |
| Partially hydrolyzed polyvinyl alcohol | 1.000 g |
| Sodium citrate | 0.146 g |
| Methyl paraben | 0.060 g |
| Propyl paraben | 0.015 g |
| Sodium edetate | 0.050 g |
| Sodium chloride | 0.715 g |
| Potassium chloride | 0.180 g |
| Sodium hydroxide | q.s. (to adjust pH to 6) |
| Hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension was aseptically dispensed into 5-15 mL plastic vessels to prepare the ophthalmic formulation.

Example 2

Ophthalmic Formulation

| | |
|---|---|
| Rebamipide | 0.100 g |
| Partially hydrolyzed polyvinyl alcohol | 1.000 g |
| Sodium citrate | 0.146 g |
| Benzalkonium chloride solution (10 w/w %) | 0.1 mL |
| Sodium edetate | 0.050 g |
| Sodium chloride | 0.715 g |
| Potassium chloride | 0.180 g |
| Sodium hydroxide | q.s. (to adjust pH to 6) |
| Hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension was aseptically dispensed into 5-15 mL plastic vessels to prepare the ophthalmic formulation.

Example 3

Ophthalmic Formulation

| Rebamipide | 0.500 g |
| Partially hydrolyzed polyvinyl alcohol | 0.500 g |
| Citric acid | 0.011 g |
| Sodium citrate | 0.146 g |
| Sodium chloride | 0.715 g |
| Potassium chloride | 0.180 g |
| Sodium hydroxide | q.s. (to adjust pH to 6) |
| Hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension was aseptically dispensed into 0.3-1 mL plastic vessels for just one use to prepare the ophthalmic formulation.

Example 4

Ophthalmic Formulation

| Rebamipide | 0.500 g |
| Partially hydrolyzed polyvinyl alcohol | 1.000 g |
| Citric acid | 0.011 g |
| Sodium citrate | 0.146 g |
| Sodium chloride | 0.715 g |
| Potassium chloride | 0.180 g |
| Sodium hydroxide | q.s. (to adjust pH to 6) |
| Hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension was aseptically dispensed into 0.3-1 mL plastic vessels for just one use to prepare the ophthalmic formulation.

Example 5

Ophthalmic Formulation

| Rebamipide | 1.000 g |
| Partially hydrolyzed polyvinyl alcohol | 1.000 g |
| Sodium citrate | 0.146 g |
| Sodium chloride | 0.715 g |
| Potassium chloride | 0.180 g |
| Sodium hydroxide | q.s. (to adjust pH to 6) |
| Hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension was aseptically dispensed into 0.3-1 mL plastic vessels for just one use to prepare the ophthalmic formulation.

Example 6

Ophthalmic Formulation

| Rebamipide | 2.000 g |
| Partially hydrolyzed polyvinyl alcohol | 1.000 g |
| Sodium citrate | 0.146 g |
| Sodium chloride | 0.715 g |
| Potassium chloride | 0.180 g |
| Sodium hydroxide | q.s. (to adjust pH to 6) |
| Hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension prepared thus was aseptically dispensed into 0.3-1 mL plastic vessels for just one use to prepare the ophthalmic formulation.

Example 7

Inhalant Formulation

| Rebamipide | 0.500 g |
| Partially hydrolyzed polyvinyl alcohol | 0.100 g |
| Chlorhexidine gluconate (20 w/w %) | 0.05 mL |
| Sodium citrate | 0.146 g |
| Sodium chloride | 0.86 g |
| Hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension was aseptically dispensed into 10-50 mL plastic or glass vessels to prepare the inhalant formulation. In case of using the inhalant formulation, 2-3 mL of the inhalant formulation should be injected into a nebulizer with a dropper, sprayed and then inhaled by a patient to be administered.

Example 8

Inhalant Formulation

| | |
|---|---|
| Rebamipide | 2.000 g |
| Partially hydrolyzed polyvinyl alcohol | 0.500 g |
| Chlorhexidine gluconate (20 w/w %) | 0.05 mL |
| Sodium citrate | 0.146 g |
| Sodium chloride | 0.86 g |
| Sodium hydroxide | q.s. (to adjust pH to 6) |
| hydrochloric acid | q.s. (to adjust pH to 6) |
| Purified water | q.s. |
| Total amount | 100 mL |

All of the above ingredients except rebamipide were dissolved in purified water with heating, the resulting solution was filtrated through an aseptic filter and then rebamipide sterilized through aseptic manipulation was added to the filtrate, and then the mixture was stirred by a magnetic stirrer to provide an aqueous pharmaceutical suspension. The aqueous pharmaceutical suspension was aseptically dispensed into 0.3-5 mL plastic vessels for just one use to prepare the inhalant formulation. In case of using the inhalant formulation, all amount of the inhalant formulation should be injected into a nebulizer, optionally diluted with other inhalant formulation or physiological saline, sprayed and then inhaled by a patient to be administered.

Example 9

Gel Formulation

| | |
|---|---|
| Rebamipide | 5.000 g |
| Partially hydrolyzed polyvinyl alcohol | 1.000 g |
| Carboxyvinyl polymer | 0.500 g |
| Benzalkonium chloride solution (10 w/w %) | 0.1 mL |
| Sodium citrate | 0.146 g |
| Sodium chloride | 0.600 g |
| Sodium hydroxide | q.s. (to adjust pH to 6) |
| Purified water | q.s. |
| Total amount | 100 mL |

The polyvinyl alcohol was dissolved in half of the predetermined amount of purified water, rebamipide was added thereto, and the mixture was stirred with a magnetic stirrer to prepare an aqueous pharmaceutical suspension. Separately, carboxyvinyl polymer was dissolved in the residual purified water, and then the other ingredients were added to the solution to prepare a solution containing carboxyvinyl polymer. And, the above aqueous pharmaceutical suspension and the above solution containing carboxyvinyl polymer were mixed wherein the pH was adjusted and the mixture was gelatinized to prepare a gel formulation. The gel formulation obtained above was filled in 3-20 mL plastic or aluminum tubes.

Example 10

Gel Formulation

| | |
|---|---|
| Rebamipide | 5.000 g |
| Partially hydrolyzed polyvinyl alcohol | 2.000 g |
| Carboxyvinyl polymer | 0.500 g |
| Benzalkonium chloride solution (10 w/w %) | 0.1 mL |
| Sodium citrate | 0.146 g |
| Sodium chloride | 0.200 g |
| Sodium hydroxide | q.s. (to adjust pH to 6) |
| Hydrochloric acid | q.s. (to adjust pH to 6) |
| Purified water | q.s. |
| Total amount | 100 mL |

The polyvinyl alcohol was dissolved in half of the predetermined amount of purified water, rebamipide was added thereto, and the mixture was stirred with a magnetic stirrer to prepare an aqueous pharmaceutical suspension. Separately, carboxyvinyl polymer was dissolved in the residual purified water, and then the other ingredients were added to the solution to prepare a solution containing carboxyvinyl polymer. And, the above aqueous pharmaceutical suspension and the above solution containing carboxyvinyl polymer were mixed wherein the pH was adjusted and the mixture was gelatinized to prepare a gel formulation. The gel formulation obtained above was filled in 3-20 mL plastic or aluminum tubes.

Example 11

Ointment Formulation

| | |
|---|---|
| Rebamipide | 0.200 g |
| Partially hydrolyzed polyvinyl alcohol | 0.100 g |
| Purified water | 0.500 g |
| Sodium chloride | 0.001 g |
| Methyl paraben | 0.060 g |
| Propyl paraben | 0.015 g |
| White petrolatum | q.s. |
| Total amount | 100 g |

Polyvinyl alcohol and sodium chloride were dissolved in purified water. Thereto rebamipide was added, and the mixture was stirred with a magnetic stirrer to prepare an aqueous pharmaceutical suspension. Alternatively, white petrolatum was warmed to be melted, and thereto methyl paraben and propyl paraben were dissolved. Optionally cooling, the aqueous pharmaceutical suspension prepared above was added to the mixture. And the mixture was homogenized to prepare an ointment formulation. The ointment formulation obtained above was filled in 3-20 mL plastic or aluminum ointment-tubes.

Experiment 1: Long-Term Stability Test

The ophthalmic formulations of Examples 5 and 6 prepared above were stored under the condition of 25° C./60% RH for 36 months, and the survival rate of rebamipide, osmotic pressure, pH, and mean particle size of rebamipide were sequentially measured. The measure of the particle size of rebamipide was carried out using a laser diffractometer (Shimadzu SALD-3000J).

As a result, in all measure time-points (i.e. before the storage and after the storage of 12, 24 and 36 months), all the results of the survival rate of rebamipide, osmotic pressure, pH, and mean particle size were satisfied with the criteria (survival rate of rebamipide was 90% or higher, osmotic pressure was 245-325 mOm, pH was 5-7, and mean particle size was 0.5-5 μm). Accordingly, it has been confirmed that rebamipide in a fine-particle state can be stored as a stable suspension of rebamipide fine particle without decomposition or agglutination under the long-term stability test.

Experiment 2: Measure of Mean Particle Size

The suspensions (Example 12 and Comparative Example 1) shown in Table 1 were prepared according to the following procedure. First of all, the ingredients other than rebamipide were warmed to be dissolved in purified water. To the solution then was added rebamipide, and the mixture was stirred at room temperature for 1 hour with a magnetic stirrer (Teflon™ stirrer 30 mm, about 500 rpm) to prepare a suspension thereof. The particle size of rebamipide in the prepared suspension was measured using a laser diffractometer (Shimadzu SALD-3000J).

TABLE 1

| Ingredient for Formulation | Example 12 | Comparative Example 1 |
| --- | --- | --- |
| rebamipide | 1.000 g | 1.000 g |
| partially hydrolyzed polyvinyl alcohol | 1.000 g | — |
| Hydroxypropylmethyl cellulose (60SH4000) | — | 0.300 g |
| Sodium citrate | 0.146 g | 0.146 g |
| Sodium chloride | 0.715 g | 0.715 g |
| Potassium chloride | 0.180 g | 0.180 g |
| Sodium hydroxide | q.s. (to adjust pH to 6) | q.s. (to adjust pH to 6) |
| Hydrochloric acid | q.s. (to adjust pH to 6) | q.s. (to adjust pH to 6) |
| Purified water | q.s. | q.s. |
| Total amount | 100 ml | 100 ml |

The results are shown in FIG. 1. The "A" in FIG. 1 indicates the particle distribution of rebamipide suspension in Example 12, and the "B" indicates the particle distribution of rebamipide suspension in Comparative Example 1. From the results, it has been confirmed that rebamipide is dispersed at the particle size of 1 μm or smaller when stirred with a magnetic stirrer in the presence of polyvinyl alcohol, and then rebamipide in the suspension is dispersed as a fine-particle state (see Table 1, A). On the contrary, it has been confirmed that rebamipide is dispersed at the particle size of 30 μm or larger when stirred with a magnetic stirrer without polyvinyl alcohol, and then rebamipide in the suspension is in an agglutinated state to form a secondary particle thereof (see Table 1, B).

According to the above-mentioned results, it has been clarified that rebamipide can be dispersed as a fine-particle state without using a special dispersing/suspending device for strong stirring when using polyvinyl alcohol.

The invention claimed is:

1. An aqueous suspension comprising fine particles of rebamipide having a mean particle size ranging from 0.2 μm to 5 μm and polyvinyl alcohol.

2. The aqueous suspension of claim 1 further comprising a sodium salt compound.

3. The aqueous suspension of claim 1 or 2 wherein rebamipide is in 0.1-30 w/v % and polyvinyl alcohol is in 0.1-4 w/v %.

4. The aqueous suspension of any one of claims 1-3, which is an ophthalmic formulation.

5. A process for the preparation of an aqueous suspension comprising rebamipide, which comprises
   (1) mixing water and polyvinyl alcohol to prepare an aqueous solution containing polyvinyl alcohol, and
   (2) adding fine particles of rebamipide having a mean particle size ranging from 0.2 μm to 5 μm to the aqueous solution containing polyvinyl alcohol and mixing to give the aqueous suspension comprising rebamipide.

* * * * *

UNITED STATES PATENT AND TRADEMARK OFFICE
CERTIFICATE OF CORRECTION

| | |
|---|---|
| PATENT NO. | : 8,772,317 B2 |
| APPLICATION NO. | : 12/447065 |
| DATED | : July 8, 2014 |
| INVENTOR(S) | : Masuda |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this
Fifteenth Day of September, 2015

Michelle K. Lee
*Director of the United States Patent and Trademark Office*